US010485673B2

United States Patent
Salunke

(10) Patent No.: US 10,485,673 B2
(45) Date of Patent: Nov. 26, 2019

(54) ARTIFICIAL IMPLANT FOR ATLAS-AXIS (C1-2) LATERAL JOINTS AND METHOD OF USE THEREOF

(71) Applicant: Pravin Salunke, Chandigarh (IN)

(72) Inventor: Pravin Salunke, Chandigarh (IN)

( * ) Notice: Subject to any disclaimer, the term of this patent is extended or adjusted under 35 U.S.C. 154(b) by 387 days.

(21) Appl. No.: 15/129,944

(22) PCT Filed: Apr. 6, 2015

(86) PCT No.: PCT/IN2015/000163
§ 371 (c)(1),
(2) Date: Sep. 28, 2016

(87) PCT Pub. No.: WO2015/155789
PCT Pub. Date: Oct. 15, 2015

(65) Prior Publication Data
US 2017/0209281 A1    Jul. 27, 2017

(30) Foreign Application Priority Data
Apr. 7, 2014  (IN) .............................. 996/DEL/2014

(51) Int. Cl.
*A61F 2/44* (2006.01)
*A61F 2/46* (2006.01)
*A61F 2/30* (2006.01)

(52) U.S. Cl.
CPC .............. *A61F 2/4405* (2013.01); *A61F 2/44* (2013.01); *A61F 2/4611* (2013.01);
(Continued)

(58) Field of Classification Search
CPC .. A61F 2/44; A61F 2/4405; A61F 2/46; A61F 2/4611
See application file for complete search history.

(56) References Cited

U.S. PATENT DOCUMENTS 7,566,346 B2     7/2009  Kirschman
9,668,772 B1 *   6/2017  Crawford ........... A61B 17/7011
(Continued)

FOREIGN PATENT DOCUMENTS

CN     2390561 Y    8/2000
CN     1669539 A    9/2005
(Continued)

OTHER PUBLICATIONS

English Abstract of JP 8-35226 A.
(Continued)

*Primary Examiner* — Christopher J Beccia
(74) *Attorney, Agent, or Firm* — Ladas & Parry LLP

(57) ABSTRACT

The joint implant of the present invention is fitted into C1-2 lateral joints through the back of the neck instead of oral approach to avoid infections. It is made of 2 inter-digitating components. One part of the joint implant has a circular railing circumference of a circle, the center of which is odontoid, that inter-digitates in a corresponding circular channel of the other part. Two such implants are fixed on both sides of C1-2 joint simultaneously along the circumference. The circular railings provide mainly circular motion in clockwise and anti-clockwise direction. With some degree of play in channel and rail and making the interacting surfaces of the implant convex on convex, provides the gyroscopic motion with lateral and translational movement and also coupling (vertical translation on rotational movement). This gyroscopic design makes it universal and is likely to work in C1-2 joints of every individual with any possible joint orientation.

14 Claims, 10 Drawing Sheets

(52) U.S. Cl.
CPC .......... *A61F 2002/3039* (2013.01); *A61F 2002/30116* (2013.01); *A61F 2002/30131* (2013.01); *A61F 2002/30383* (2013.01); *A61F 2002/30392* (2013.01); *A61F 2002/30397* (2013.01); *A61F 2002/30578* (2013.01); *A61F 2002/30621* (2013.01); *A61F 2002/30825* (2013.01); *A61F 2002/30904* (2013.01); *A61F 2002/448* (2013.01)

(56) References Cited

U.S. PATENT DOCUMENTS

| | | | |
|---|---|---|---|
| 2007/0123863 A1 | 5/2007 | Winslow et al. | |
| 2007/0260318 A1* | 11/2007 | Lawson | A61F 2/442 623/17.16 |
| 2008/0306597 A1 | 12/2008 | Adamo | |
| 2013/0131726 A1* | 5/2013 | Suh | A61B 17/7064 606/249 |

FOREIGN PATENT DOCUMENTS

| | | | |
|---|---|---|---|
| CN | 1973785 A | 6/2007 | |
| CN | 20112126393 U | 1/2012 | |
| CN | 103142331 A | 6/2013 | |
| JP | 8-35226 A | 6/1998 | |
| WO | 2011/012705 A1 | 2/2011 | |
| WO | WO-2011012705 A1 * | 2/2011 | ............. A61B 17/70 |
| WO | 2012/1021592 A2 | 2/2012 | |
| WO | 2012/145971 | 11/2012 | |
| WO | 2013/177314 A1 | 11/2013 | |

OTHER PUBLICATIONS

English Abstract of CN 20112126393 U.
English Abstract of CN 1669539 A.
English Abstract of CN 1973785A.
English Abstract of CN 2390561Y.
English Abstract of CN 103142331A.
Bin Lu et al.; Artificial atlanto-odontoid joint replacement through a transoral approach; Eur Spine J (2009) 18:109-117.

* cited by examiner

FIG. 9c(1)

ARTIFICIAL IMPLANT FOR ATLAS-AXIS (C1-2) LATERAL JOINTS AND METHOD OF USE THEREOF

RELATED APPLICATION

This application is a national phase entry under 35 USC 371 of International Patent Application No.: PCT/IN2015/000163 filed on 6 Apr. 2015, which claims priority from India Application No. 996/DEL/2014 filed on 7 Apr. 2014, the disclosures of which are incorporated in their entirety by reference herein.

FIELD OF INVENTION

The present invention relates generally to the field of implants and instrumentation used in neurological surgeries. It pertains to an artificial implant for atlas-axis (C1-2) lateral joints and method of use thereof. Recently, artificial discs have been introduced to preserve motion without compromising the stability. This invention pertains to an artificial implant in the form of a joint or a dynamic stabilizer for the lateral atlas-axis (C1-2) joints.

BACKGROUND OF THE INVENTION

Anatomical Terms: (Refer FIG. 1, FIG. 2 and FIG. 3)

Atlas (C1):

It is the most superior (first) cervical vertebra of the spine which supports the globe of the head. The Atlas' chief peculiarity is that it has no body, it is ring-like, and consists of an anterior and a posterior arch and two lateral masses.

Axis (C2):

It is the second cervical vertebra of the spine and is named the axis or epistropheus. It forms the pivot upon which the first cervical vertebra (C1—the atlas), which carries the head, rotates. The most distinctive characteristic of this bone is the strong odontoid process ("dens") which rises perpendicularly from the upper surface of the body. That peculiar feature gives to the vertebra a rarely used third name: vertebra dentata.

The atlas along with the Axis forms the joint connecting the skull and spine. The atlas and axis are specialized to allow a greater range of motion than normal vertebrae. They are responsible for the nodding and rotation movements of the head.

The Atlas and Axis are important neurologically as it houses the cervico-medullary junction that is packed with vital neural structures.

Dens or Odontoid Process:

It exhibits a slight constriction or neck where it joins the body. The dens acts as a pivot that allows the atlas and attached head to rotate on the axis, side to side.

Occipital Bone:

It is a saucer-shaped membrane bone situated at the back and lower part of the cranium, is trapezoidal in shape and curved on itself. It is pierced by a large oval aperture, the foramen magnum, through which the cranial cavity communicates with the vertebral canal.

Atlanto-Occipital Joint:

It is the articulation between the atlas and the occipital bone and consists of a pair of condyloid joints. The atlanto-occipital joint is a synovial joint which allows the head to nod up and down on the vertebral column.

Atlanto-Axial Joint:

It is a joint in the upper part of the neck between the first and second cervical vertebrae; the atlas and axis. The atlanto-axial joint is of a complicated nature. It consists of no fewer than four distinct joints. It provides a significant range of movements (majority of the rotational movement of neck). There is a pivot articulation between the odontoid process of the axis and the ring formed by the anterior arch and the transverse ligament of the atlas. There are two lateral atlanto-axial joints that are relatively flat, unlike the other vertebral articulations thereby, providing the rotational movement between C1 with head and C2, apart from providing support. Besides this, there is minimal translational, vertical and lateral bending movements that can occur between C1-2. Vertical movement of C2 within C1 occurs with rotation of C1 over C2. This is known as coupling. With coupling, dens is at its summit with C1 and C2 in neutral position and it is at its lowest point with C1 rotated over C2 to either side. The coupling movement makes the C1-2 joint extremely efficient.

About Atlanto Axial Dislocation (AAD):

The translational movement between C1-2 is restricted by the C1 anterior arch (anteriorly) and the transverse ligament (posteriorly). The ligaments and the joint capsule of lateral atlanto-axial joints, prevents excessive rotation and lateral displacement. The orientation of facets of C1-2 lateral masses prevents vertical dislocation. Atlanto axial dislocation is a condition in which, there is abnormal displacement between C1 and C2 in single or more than one plane. This dislocation is in short labeled as AAD. Such dislocation may be reducible (correctable on neck movement in a direction opposite to the displacement) or irreducible. A major risk in the case of AAD is spinal cord compression, which can cause severe neurological injuries.

Causes for AAD:

The causes vary from congenital (abnormal orientation of the joints seen in individuals born with deformed joints), ligamentous laxity due to infection or its squeale, inflammatory diseases like rheumatoid arthritis or trauma leading to fracture of the restricting odontoid.

Symptoms of AAD:

Pain in the neck area, especially in the back of head and neck. Movement is painful and restricted. Spinal cord compression is a major risk in this event. The odontoid process may compress the spinal cord, causing severe neurological injuries and even death. Neurological damage may cause change in walking ability, weakness in the arms and legs, loss of bladder or bowel control and difficulty in breathing. Displacement and neck movements must be avoided at all costs.

Treatment for AAD:

Strict immobilisation of the neck is of paramount importance. Treatment includes symptomatic measures and cervical immobilisation in reduced position, usually beginning with a rigid cervical collar. Close monitoring of the patient is essential due to the risk of displacement of the neck bones, potentially causing spinal cord compression and neurological damage. Pain killers are advised for the pain. Surgery may be needed to stabilize the spine. (Ref: http://www.m-dhil.com/atlanto-axial-dislocation-symtoms-and-treatent/)

As discussed above, AAD may cause neural compromise. Therefore sometimes surgical intervention becomes a necessity.

A neurosurgeon has following options for treating AAD:

1. Reduction/removal of neural compression followed by C1-2 fusion

2. Direct reduction of C1-2 joints and fusion of C1-2 lateral joints

C1-2 fusion with cable fixation (after reduction, either by maneuvering the neck position in reducible AAD or cervical traction or by joint distraction in the irreducible variety)

C1-2 transarticular screw fixation

C1-2 lateral mass/isthmus fixation

3. Odontoid screw fixation (cases of acute trauma with non-comminuted fracture of dens)

4. Implanting an artificial atlanto-dental joint

Limitations of Above Methods:

Fusing the C1-2 Lateral Joints:

Most of the techniques are directed at fusing the C1-2 lateral joints in reduced position that avoids further dislocation. However, such fusion leads to gross restricting of the neck movements. Such restricted movement hampers a person's daily activity like driving, playing outdoor games that require rotational movement of the head.

Artificial Atlanto-Dental Joint:

Although this is physiological and provides stability without compromising the neck movements. However, the ONLY possible way to fix such central joint is through the oral cavity that is potentially infected and therefore is not desirable. Furthermore, use of such joint is not feasible in congenital anomalies that have oblique C1-2 lateral joints or in inflammatory diseases like rheumatoid arthritis where the vertical settling is of common occurrence along with dislocation. Additionally, it cannot provide the lateral or translational movements.

Proposed Solution by the Inventor:

The inventor being a neurosurgeon himself, has designed and developed an implant which could reduce if not eliminate totally, the drawbacks of presently available implants or fusion techniques and the patient can have better mobility of the neck and therefore better quality of life. This implant is in the form of an artificial joint or a dynamic stabilizer for the lateral atlas-axis (C1-2) joints.

Advantages of the Present Invention:

1. Stability of C1-2 without Compromising the Neck Movements:

The artificial lateral C1-2 joints would provide good stability without compromising the normal movements of neck i.e., axial rotation close to normal, small degree of lateral tilt and minimal translational movement in anteroposterior and lateral direction (multiple degrees of freedom)

2. Avoiding the Infected Route:

The placement of artificial C1-2 lateral joints of the present invention is through the back of neck, thereby avoiding the infected cavity.

3. Use in Congenital Anomalies:

The approach requires opening of lateral C1-2 joints and drilling the facetal surfaces flat and close to normal. The inventor remodels a deformed joint as close to a normal joint as possible. Following the drilling, it is feasible to use the implant in most of the cases of congenital AAD.

4. Use in Inflammatory Arthritis

Settling is often seen in cases of AAD due to rheumatoid arthritis. The new implant is likely to increase the height apart from providing dynamic stabilization 5. Providing the Naturally Occurring Lateral and Translational Movement with Coupling to Make it the Most Efficient.

The implant has been designed to provide coupling and minimal translational movement. This allows more degrees of freedom of movement and makes it efficient.

6. Universal Design

The implant can be fixed in any individual with AAD irrespective of the angles and orientation of C1-2 joints As is clear from the above, instead of modifying the techniques of lateral C1-2 joint fusion or focusing on the placement of artificial atlanto-dental joint through a potentially infected cavity, inventor came up with very practical solution of providing stability of C1-2 joints without restricting the neck movements. Furthermore, it does not use the infected route and can be used in patients with congenital anomalies or inflammatory arthritis.

Prior Art and its Drawbacks:

Various doctors and researchers have been working to solve the problem as cited above. The approaches used are discussed in the patents below:

| S No | Patent application no. | Disadvantage of prior art invention | Comparison with present invention |
|---|---|---|---|
| 1. | WO2012145971 | The ONLY possible way to fix such central joint is through the oral cavity that is potentially infected, Cannot be used in deformed C1-2 joints (congenital AAD and Basilar invagination) or inflammatory AAD with settling. Does not provide the naturally occurring translational and coupling movement reducing the axial freedom of movement | The present invention is fixed through the back of the neck and not through oral cavity thereby reducing the post-operative infection. Can be used in Congenital and inflammatory AAD Does provide the naturally occurring translational and coupling movements more degrees of freedom). |
| 2. | WO2013/177314A1 | This implant is bulky in nature. It is difficult to be used in congenital Irreducible Atlantoaxial dislocation as it reduction would require opening and drilling of joints. Furthermore the tendency is to get dislocated in anteroposterior direction due to obliquity, producing a constant drag on the implant. It provides minimal rotational movement and is likely to be | The present invention requires opening of joints, scraping of the cartilage and even drilling it flat in case of oblique shape (congenital variety or traumatic locked facets) to accommodate the implant. This helps in reduction of joints. The implant is not bulky and placed through posterior approach thereby avoiding the potentially infected cavity. Also the artificial joint replaces |

-continued

| S No | Patent application no. | Disadvantage of prior art invention | Comparison with present invention |
|---|---|---|---|
| | | restricted further due to soft tissue entanglement. Normal C1-2 lateral joints are a pre-requisite for this implant. The placement of this device is through standard posterior approach to cervical spine. | the natural joint making it more physiological, avoids the soft tissue and provides greater range of movement. |
| 3. | CN 1669539 A | Again it uses the potentially infected trans-oral route for placement. The hook with sheet replaces the transverse ligament and is connected to the C1 lateral mass on one side. The hook requires intact dens and of course anatomically normal C1-2 joints | The route is surgically clean. Also, though an intact dens provides a good stability. However, even in its absence or destruction or hypoplasia, the rail road would allow action only in rotational plane and is stable. Also, it can be used in oblique lateral C1-2 joints. |
| 4. | CN1973785A | The ONLY possible way to fix such central joint is through the oral cavity that is potentially infected. Only rotational movement is possible | The present invention is fixed through the back of the neck and not through oral cavity thereby reducing the post-operative infection. Multiple degrees of freedom of movement |
| 5. | CN2390561Y | The ONLY possible way to fix such central joint is through the oral cavity that is potentially infected. Only rotational movement is possible | The present invention is fixed through the back of the neck and not through oral cavity thereby reducing the post-operative infection. Multiple degrees of freedom of movement |
| 6. | CN103142331A | It is a fusion device. Can provide stability but at the cost of mobility | Use of present invention allows the patient to have better mobility of the neck. |
| 7. | US7566346 | Use in sub-axial cervical spine. Provides rotation and translational movement both in lateral and antero-posterior direction (three degrees of motion). This cannot be used in C1-2 lateral joints as the rotational motion required is in around the odontoid that acts as a pivot and not around the joint itself. Even if the channel is made circular for the ball, the structure of artificial joint makes it risky for lateral and vertical dislocation. | The intended design is to provide all degrees of freedom of movement as provided by the natural C1-2 lateral joints. The unique rail and channel architecture on the periphery with some play and the central gyroscopic design makes it stable with significant freedom of movement with leading to antero-posterior, lateral and vertical dislocation. |
| 8. | US20070123863 | This provides the spacer effect, providing vertical distraction and with preservation of some movement translational, angular and rotational movement. But the degree of movement available cannot be utilized in C1-2 lateral masses as it is minimal. The excess lateral and angular movement provided by the artificial facets is dangerous at C1-2 level | The present design provides maximum movement in rotational plane and with naturally occurring lateral or angular movement along with coupling. |

CITED PUBLICATION

Bin Lu Xi Jing He, Chen Guang Zhao, HaoPeng Li, and Dong Wang; Artificial atlanto-odontoid joint replacement through a transoral approach; Eur Spine J (2009) 18:109-117.

To avoid the loss of rotation that follows odontoid process resection with anterior and/or posterior stabilization, a new type of two-piece, metal-on-metal, artificial atlanto-odontoid joint is designed which when implanted onto a decompressed specimen allowed the relocation of the axis of rotation to the artificial joint through the transoral approach.

In comparison, the present invention is fixed through the back of the neck and not through oral cavity thereby reducing the post-operative infection.

Hence it is clear that none of the available patents/publications or commercially available implants is similar to the one disclosed in the present invention.

Objects of the Present Invention

1. The main object of the present invention is to disclose an atlanto-axial joint implant which can give freedom of movement to the neck close to natural movement.
2. Another object of the present invention is to disclose an atlanto-axial joint implant which can be fitted through the back of the neck instead of oral approach to avoid infections.
3. Yet another object of the present invention is to disclose an atlanto-axial joint implant which can also be used for treating atlanto-axial dislocation due to congenital abnormalities or inflammatory arthritis with settling apart from traumatic atlanto-axial dislocation.

SUMMARY OF THE INVENTION

The odontoid process of C2 acts as a pivot around which the C1 (atlas) rotates. The pair of lateral atlanto-axial joints is flat thereby providing support. The flat surfaces aid in the movement. These lateral atlanto-axial joints lie along the circumference. So the movement occurs simultaneously in both lateral joints either in clockwise or anti-clockwise direction. The movement is limited by ligaments. Occasionally, the ligaments become lax or the joints are oblique or the odontoid is fractured. This makes both the C1 facets slip over C2 facets but in the same direction rather than in a circular motion. In cases of congenital AAD, the joints are deformed and abnormal orientation of facets gives rise to dislocation.

The present joint implant fixes into C1-2 lateral joints. It is made of 2 inter-digitating components. One part of the joint implant has a circular railing that inter-digitates in a corresponding circular channel of the other part. The railing and the channel is along the circumference of a circle, the center of which is odontoid. Such implants are fixed on both sides of C1-2 joint simultaneously along the circumference. The circular railings provide mainly circular motion in clockwise and anti-clockwise direction. If the channel and rail have no play or tolerance, it cannot allow any other motion except axial rotation. This provides stability in atlanto-axial joint without compromising the circular motion. The rail and channel are on the periphery and sideways with some play; in the primary proposed embodiment. The interacting surfaces of the implant are convex on convex to provide the gyroscopic motion with lateral and translational movement and most importantly coupling (vertical translation on rotational movement).

DETAILED DESCRIPTION OF THE INVENTION

Figure 1:
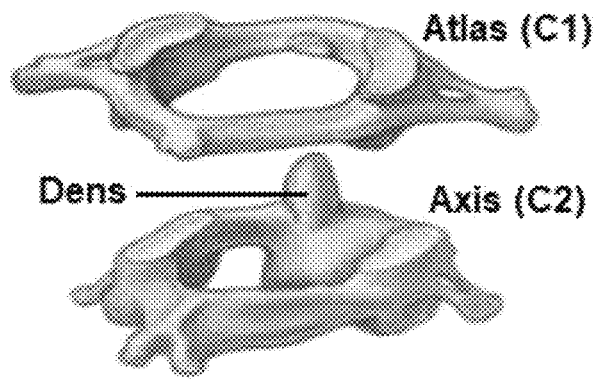
FIGS. 1, 2, 3 and 4: Anatomical figures of the joints C1-C2

The movement of the neck can be in two directions—Up and Down as well as Left and Right.

The dens or the Odontoid Process of AXIS C2 acts as a pivot that allows the atlas (C1) and attached head to rotate on the axis, side to side i.e Movement of neck in Left and Right directions.

The atlanto-occipital joint is a synovial joint which allows the head to nod up and down on the vertebral column i.e movement of neck in Up and Down directions.

Atlanto-axial joint is a complicated joint in the upper part of the neck between the first and second cervical vertebrae; the atlas (C1) and axis (C2).

It provides a significant range of movements. There is a pivot articulation (PA of FIG. 1) between the odontoid process of the axis (C2) and the ring formed by the anterior arch and the transverse ligament of the atlas (C1). There are two lateral atlanto-axial joints (LAJ of FIG. 1) that are relatively flat, slightly slanting downwards, unlike the other vertebral articulations thereby, providing the rotational movement between atlas (C1) with head and axis (C2), apart from providing support. Besides this, there are minimal translational, vertical and lateral bending movements that can occur between C1-2 because of the anatomical flat (in one vertical plane [x-z axis]) and slightly slanting shape (in the other vertical plane [y-z plane]) of lateral atlanto-axial joints.

Therefore, as is obvious now, the Atlas (C1), Axis (C2) and the Atlanto axial joint between C1 and C2 is responsible for majority of the neck movements. Any abnormal displacement between C1 and C2 in single or more than one plane (called AAD) due to congenital reasons or trauma or ligament laxity, can cause restriction in neck movement or sometimes even spinal cord compression thereby causing neurological injuries too.

Sometimes the Atlas (C1) slips over the Axis (C2). Since the pair of lateral atlanto-axial joints lying around the circumference are flat to help in the movement of neck in either in clockwise or anti-clockwise direction. This movement is limited by ligaments. Occasionally, the ligaments become lax or the joints are oblique or the odontoid is fractured. This makes the C1 slip over C2 but in the same direction rather than in a circular motion.

To overcome this restriction in neck movement and to reduce complications due to AAD, the implant of the present invention does not use fusion techniques which permanently restrict the movement of neck to avoid further neurological complications nor does it uses odontoid screw fixation. It also does not use fixing an atlanto-dental joint as these methods have limitations mentioned in the preceding text.

The implant of the present invention fixes into C1-2 lateral joints avoiding the use of oral infection prone route.

Unlike ball and socket joint having a limitation of slipping off vertically, the inventor has developed a novel implant in the form of a joint which can be so fitted along the circumference of a circle, the center of which is odontoid such that it can mimic the natural neck and head movement in clockwise and anticlockwise direction.

In a preferred embodiment (FIG. 6), the present implant is made of 2 inter-digitating components called Circular rail (CR1L) suitable for fixing in atlas (C1) and Circular channel (CC2L) for fixing into axis (C2). On the edge of CC2L there is a circular channel at 60 degrees to the surface which corresponds to railing on the edge of CR1L. The rail and the channel is along the circumference of a circle, the center of which is the odontoid. Such circular rails can provide circular motion in clockwise and anti-clockwise direction. The locking pins (LP and LP2) of CC2L on each side prevent slipping of CC2L and CR1L to sides or excessive translational motion. This provides stability in atlanto-axial joint without compromising the circular motion.

Figure 6:
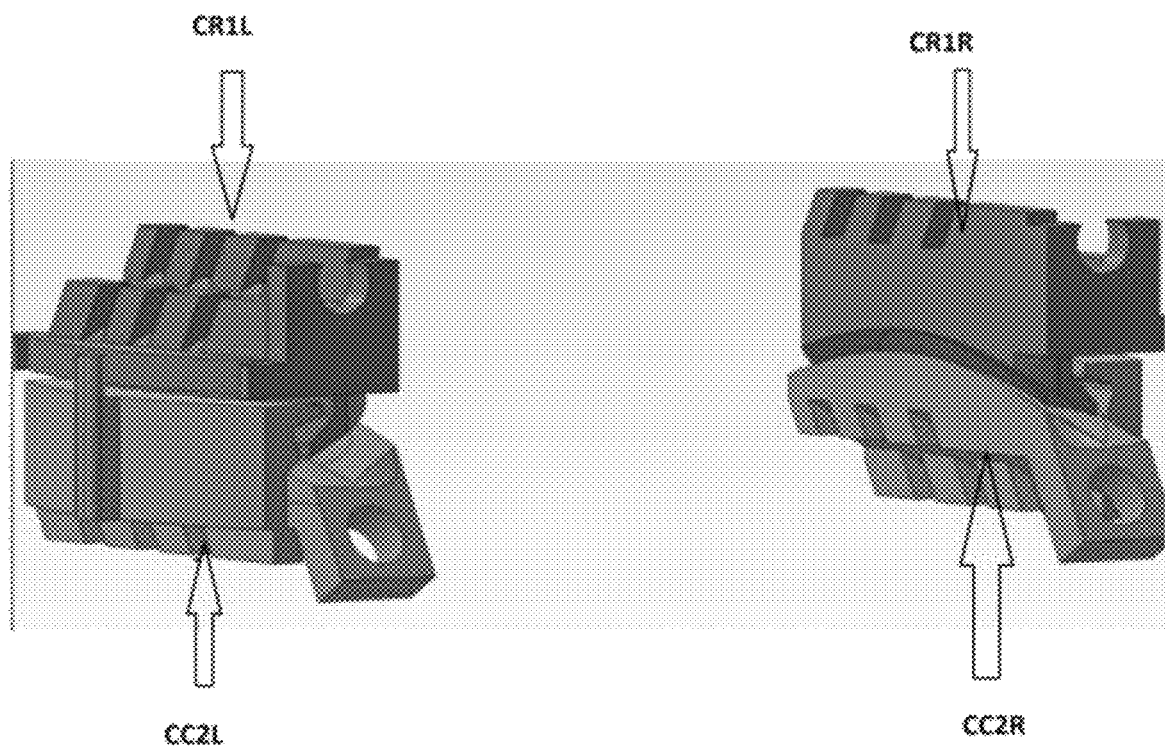
FIG. 6: Complete Assembly of the present invention suitable for both sides of human C1-2 lateral joints as seen from behind and left side.
  CR1L: Component to be fixed in leftatlas (C1)
  CC2L: Component to be fixed in left axis (C2)
  CR1R: Component to be fixed in right atlas (C1)
  CC2R: Component to be fixed in right axis (C2)
  FIG. 6A:—Exploded view of CR1L component of FIG. 6
  FIG. 6A1:—Right side view
  UL: Upper ledge of CR1L
  ULo: Outer edge of upper ledge (UL)
  ULi: The inner edge of the upper ledge (UL)
  LL: Lower ledge of CR1L
  CONC: Concave undersurface of LL conforming to basic cone on cone design
  CONV: Additional Convex surface to make the design gyroscopic and reducing contact point to one
  FIG. 6A2:—Right Top view
  LP: Locking Pin
  R: Ridge for securing implant within bone inhibiting any movement within bone and implant
  Ri: Inner ridge
  Ro: Outer ridge
  MR: Monorail to loosely fit into CC2 components channel
  TR: Trapezoid
  FIG. 6A3:—Rear Bottom view
  LP: Locking Pin
  CS: Connecting stalk
  G: Groove
  FIG. 6A4:—Rear Top view
  P1: Plate to fix on the posterior surface of CR1 facet with hole for screw fitting
  H1: Hole to fix screw
  ULo: Outer edge of upper ledge (UL)
  MR: Monorail [outer edge of lower ledge (LL)] to loosely fit into CC2 components channel
  FIG. 6B:—Exploded view of CC2L component of FIG. 6
  FIG. 6B1:—Right side view
  UL2: Upper ledge of CC2L
  UL2i: Inner edge of upper ledge (UL2)
  LP2: Locking pin
  CONV2: Convex surface conforming to Concave surface CONC of CR1L
  CONV3: Additional convexity makes the design gyroscopic and reducing contact point to one with C1 Convex component
  FIG. 6B2:—Left Side Rear Bottom view
  UL2o: Outer edge of the upper ledge (UL2)
  W1: Wall on one side of the outer edge (UL2o)
  FIG. 6B3:—Right Side Rear Top view
  CMR: Channel in W1 that houses the monorail (MR) of CR1L
  P2: Plate to fix on the posterior surface of facet with hole for screw fitting
  H2: Hole to fix screw
  FIG. 6B4:—Right Side Rear Bottom view
  RLi: Inner ridge
  RLo: Outer ridge
  LL: Lower surface of lower ledge
  FIG. 7A—Tool (T1) in the form of graduated broach for making rough cuttings in CR1 and CC2 facets.
  US1—Upper surface of graduated broach for ridges of CR1
  LS1—Lower surface of graduated broach for ridges of CC2
  UA1—Arm 1 of graduated broach
  UA2—Arm 2 of graduated broach
  CB1—Cuboids at 30 degree to horizontal
  B1—graduated broaches for ridges of CR1 at upper surface (US1)
  B2—graduated broaches for ridges of CC2 on lower surface (LS1).

Two such implants as indicated in FIG. 6 (CR1L & CC2L, CR1R & CC2R) are fitted on left and right sides of both C1-2 joints.

Design and Constructional Features of CR1

FIG. 6 A shows CR1L component viewed from various angles and its parts are marked to understand the purpose.

Figure 2:
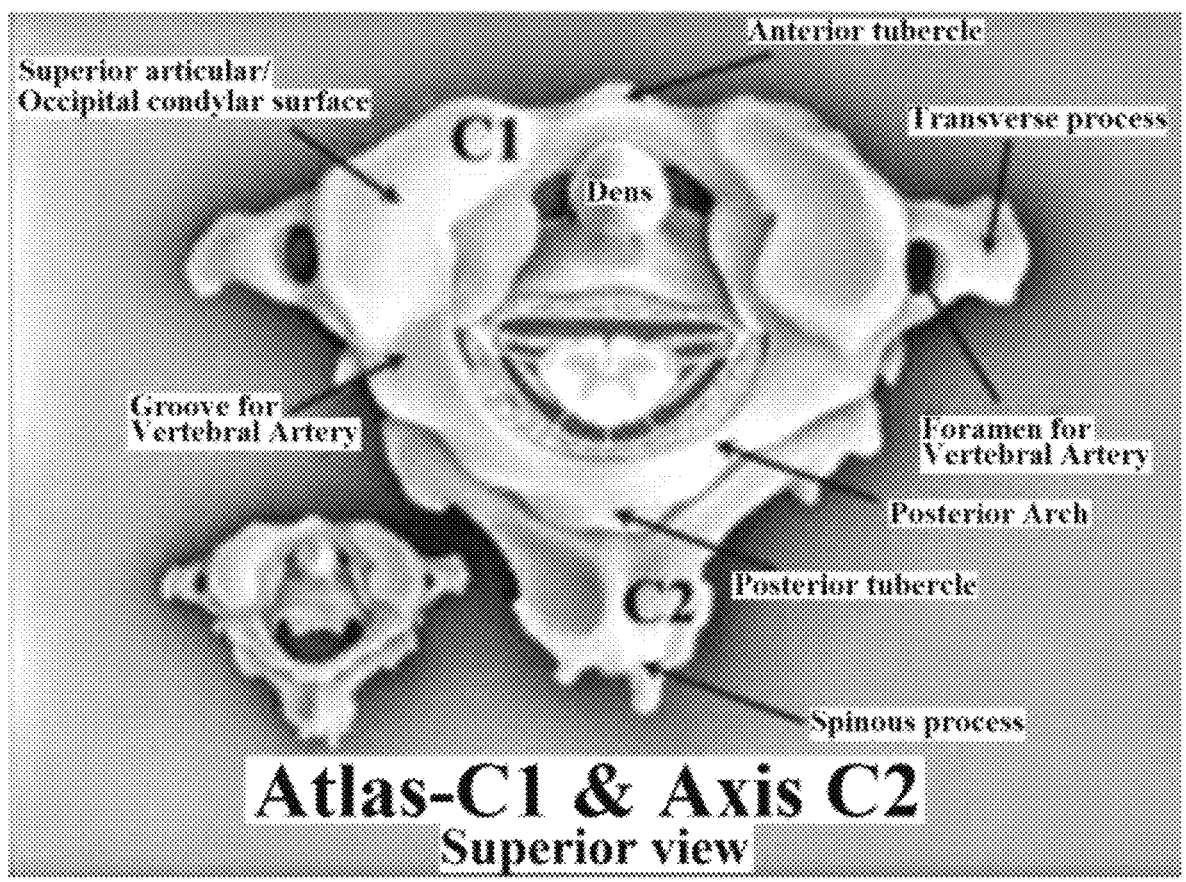
Figure 3:
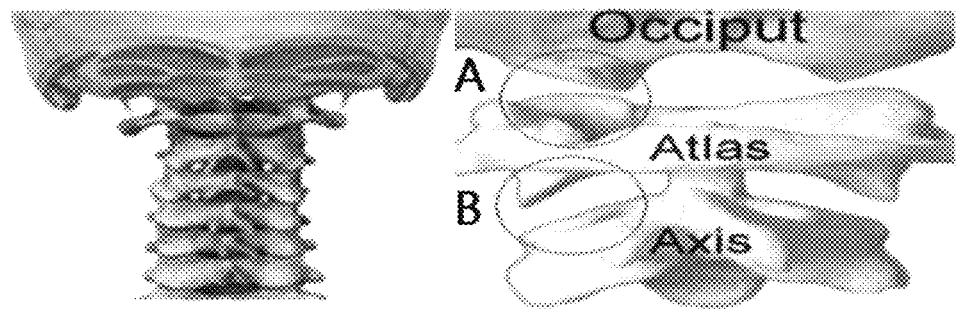
Figure 4:
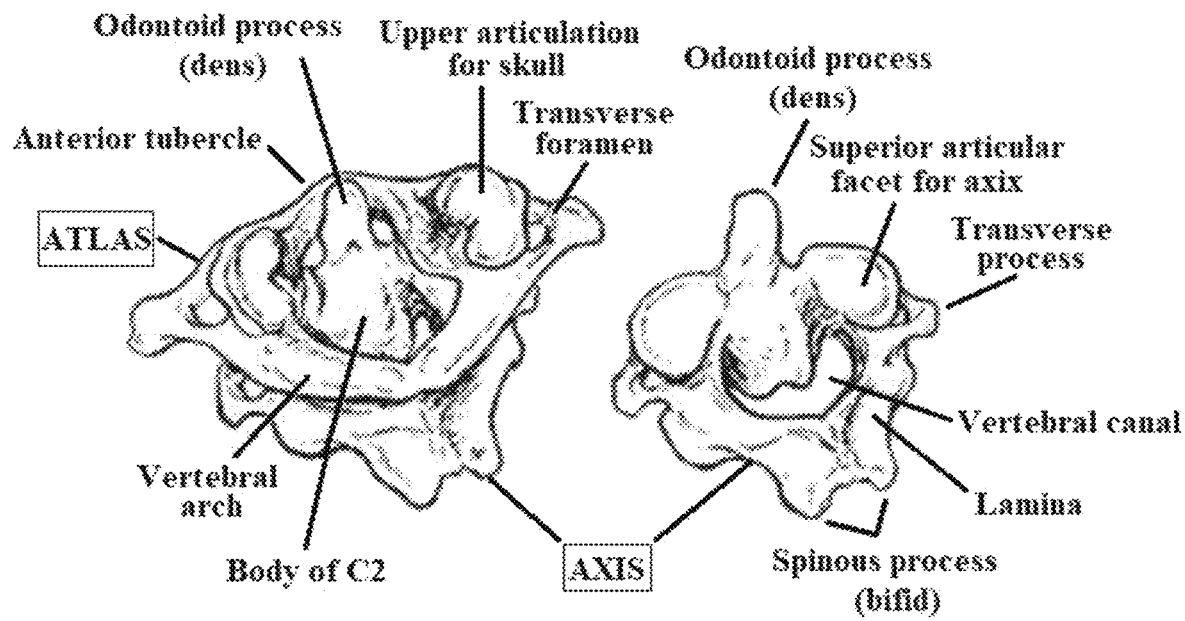
Figure 5:
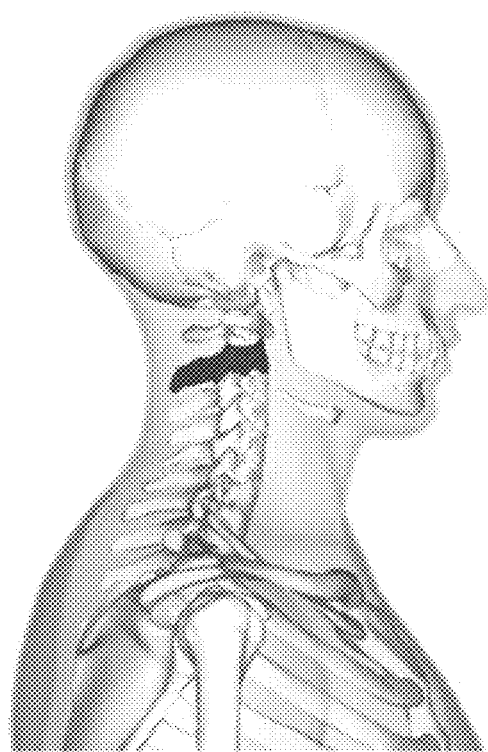
FIG. 5: Actual location of C1-C2 Joints in human neck
Figure 6A:
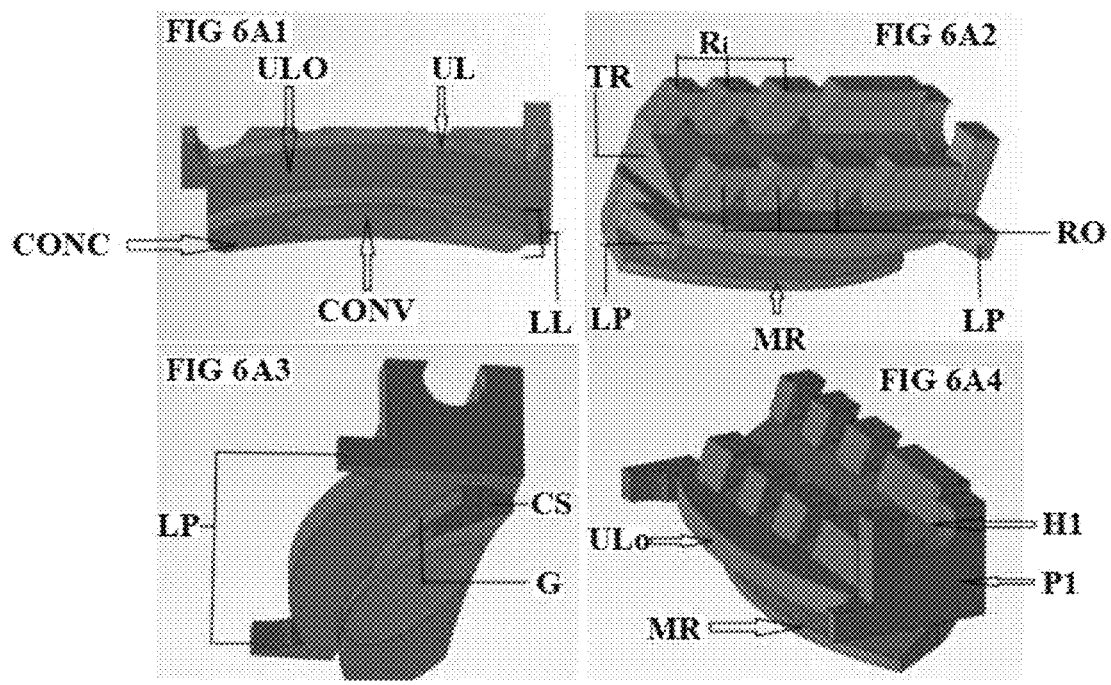

The inner edge (ULi) of the upper ledge (UL) is straight whereas the outer edge (ULo) of the upper ledge (UL) is circular, corresponding to the circumference of circle with radius of about 20-23 mm depending on the size used (center of this imaginary circle is odontoid. Although the outer edge of the lower ledge (LL) is circular, yet it is not a solid circle but consists of a groove (G) and a monorail (MR), tapering with minimal width of about 0.6 mm which gets loosely fitted into the channel in CC2L component. The MR is along the circumference of a circle with radius 18-21 mm. The inner edge (ULi) of the upper ledge (UL) is connected to lower ledge bearing concave (CONC) undersurface with 3 mm thick connecting stalk (CS). The upper surface of upper ledge (UL) is consists of ridges (R) which have thickness and height of 2 mm each, running along its entire length at 60 degrees from the surface (perpendicular to plane of ground) as shown in FIG. 6A2. Due to the shape of trapezoid (TR) (FIG. 6A2), outer ridges (Ro) are positioned lower than the inner ridges (Ri) so as to conform to the angle of C1 facet in y-z plane. These ridges (Ro & Ri) fix inside the atlas (C1) facets and prevent torsional movement. The ends of the outer edge (ULo) of upper ledge (UL) bear two projections or the locking pins (LP) that stop the implant at maximum rotation. On one of the ends of the length, the upper edge (UL) has a perpendicular plate (P1) measuring 1.5 mm thick and 3.5×3.5 mm length and breadth with ⅔ of hole (H1) on top portion. This plate (P1) would abut on the surface of facet of atlas (C2). The hole (H1) houses a 2.7 mm screw that would fix the plate (P1) into the lateral mass.

The inferior or under surface of CR1L is concave (CONC) with central spherical projection (CONV) of about 1.5 mm height on this surface. This central spherical projection (CONV) measures about 6 mm in length and 4 mm in width. Only this central spherical projection (CONV) comes in actual contact with convex upper surface of CCL2 during movement.

Design and Constructional Features of CC2L

Figure 6B:
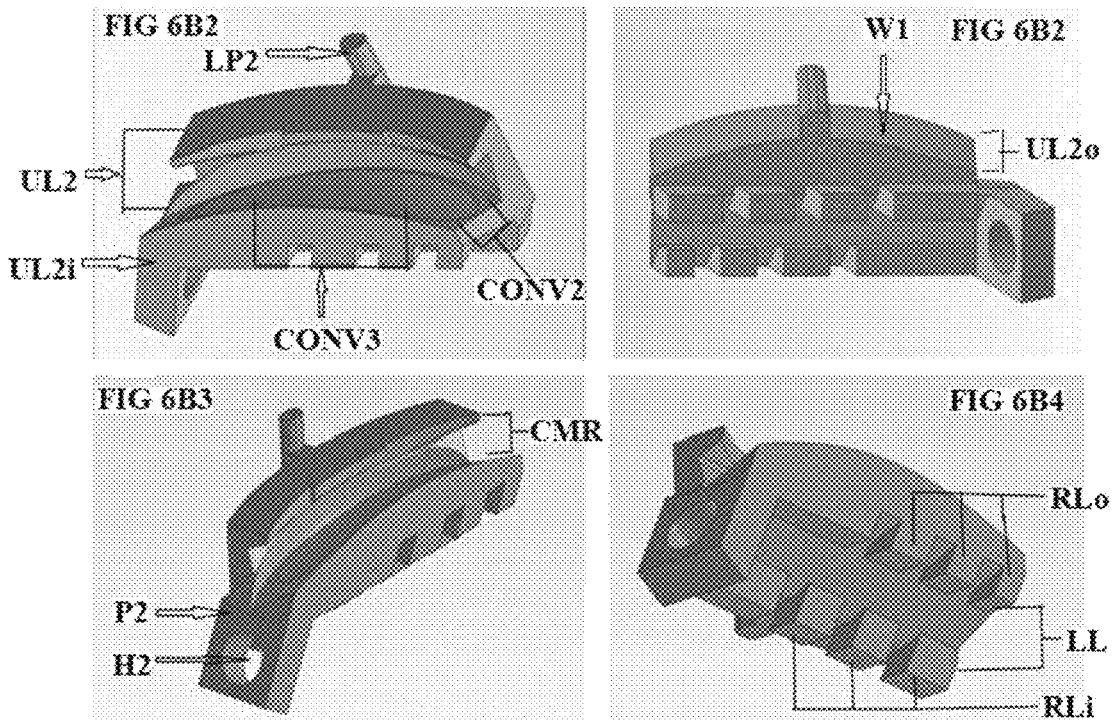

Referring to FIG. 6B, the upper ledge (UL2) of this component has slightly convex surface. The inner edge (UL2i) of the upper ledge (UL2) is straight with 16 mm length and whereas the outer edge (UL2o) of the upper ledge (UL2) is circular, corresponding to the circumference of circle with radius of about 20-23 mm depending on the size used (odontoid as center). On one side of the outer edge (UL2o) is a wall (W1) of 2.5 mm thickness and 2.5 mm height and is angulated at 60 degrees with respect to the plane of base of CCL2d. This wall (W1) has a channel (CMR) that houses the monorail (MR) of CR1. The channel (CMR) is narrowest at the center and broadens along the outer lengths of its circumference. The channel's (CMR) upper surface has upward projection in the midpoint of outer edge of its circumferences which acts as locking pin (LP2) and rotation would stop where this locking pin (LP2) touches the locking pin (LP) of CR1L. At the end of the inner edge (UL2i) of the upper ledge (UL2), there is a plate (P2) of 1.5 mm thickness and 4.2×4.2 mm width and height with hole (H2). This plate (P2) is angled at 60-70 degrees w.r.t to the plane of ground. This corresponds to the normal angle between isthmus of axis and its facet. The lower surface of lower ledge (LL) consists of ridges (RLo and RLi) which have thickness and height of 2 mm each, running along its entire length at 60 degrees from the surface (perpendicular to plane of ground). The outer ridges (RLo) are positioned higher than the inner ridges (RLi). These ridges fix inside the axis (C2) facets and prevent torsional movement. The upper surface of CCL2 is convex (CONV 2). There is an additional 0.6 mm convex (CONV 3) component added to CONV 2 which interacts with the CONV surface of C1.

Design and Constructional Features of Entire Assembly

CR1 on right and left sides, inter-digitates with the CC2 on each side. The assembly has been shown in FIG. 6(CR1L & CC2L, CR1R & CC2R). The rotational movement is in unison. It can be clockwise or anticlockwise approximately 23 degrees on either side. The movement at its maximum limit is restricted by the locking pins (LP and LP2). The play provided between the monorail (MR) (edge of lower ledge of CR1) and the channel (CMR) of CC2 on each side provides some degree of translational and angular movement. The excessive translational and angular movements are restricted by the CC2's channels on each side. The convex on convex surface makes the design gyroscopic. This makes it universal as the angles of C1-2 joint in coronal plane (y-z, vertical plane passing through both the C1-2 joints) are variable from 15-45 degrees. With angles the rotational movement is along a conical plane. Conforming to this natural path created, the design has a basic cone on cone pattern (undersurface of CR1 and upper surface of CC2). The small spherical surfaces (CONV and CONV 3) added to these interacting surfaces converts a cone on cone to a sphere on sphere model. This makes the design gyrospcopic and adaptable to the varying coronal angles in individuals. The design is deemed to work even in extreme cases, where the coronal angles may be 60 degrees or as flat as 0-5 degrees.

The sphere on sphere model also provides the coupling action existent in nature. This makes the present invention (artificial C1-2 lateral joints) as close to the natural C1-2 joint as possible.

Design and Constructional Features of the Tools Used:

Two tools are used to fix the entire implant in the form of a joint.

Figure 7A:
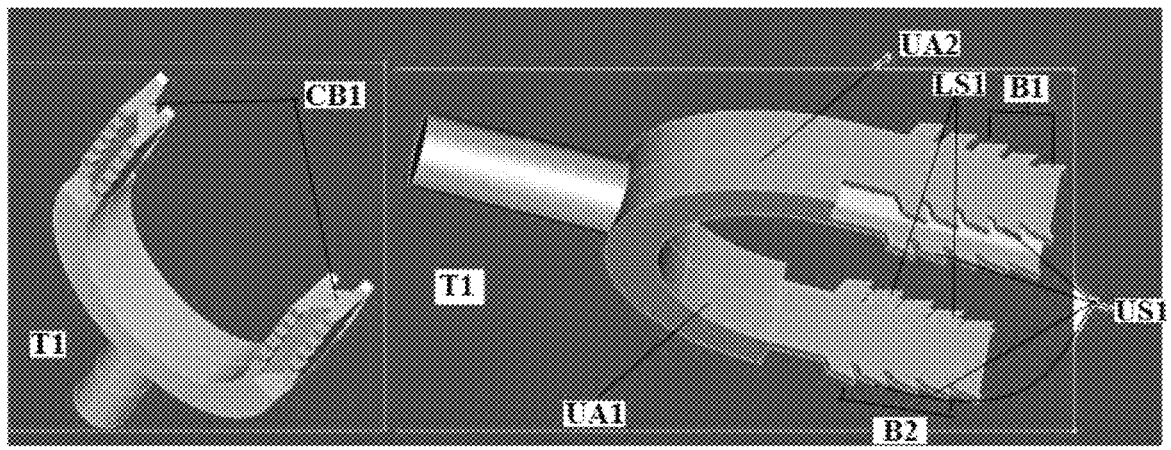
FIG. 7B—Tool (T2) in the form of regular broach for making final cutting of grooves in CR1 and CC2 facets.
  US2—Upper surface of regular broach for ridges of CR1
  LS2—Lower surface of regular broach for ridges of CC2
  UA21—Arm 1 of regular broach
  UA22—Arm 2 of regular broach
  CB2—Cuboids of regular broach at 30 degree to horizontal
  BR1—regular broaches for ridges of CR1 at upper surface (US2)
  BR2—regular broaches for ridges of CC2 on lower surface (LS2)
  FIG. 8—Figure of embodiment of the present invention
  CCL1—Circular Connector Leg 1 to be fitted on the AXIS
  CCL2—Circular Connector Leg 2 to be fitted on ATLAS

One tool (T1) is a hand tool (FIG. 7A) with two arms (UA1 and UA2) for making rough cuttings in CR1 and CC2 facets. Both the ends of arms (UA1 and UA2) are 5 cm long and 18 mm wide apart from each other and terminate as cuboids (CB1). These cuboids (CB1) which are at an angle of 30 degrees to the horizontal and are sized about 17 mm in length, 7 mm height and 8 mm wide. The inner edge of cuboids (CB1) is higher up than the outer on either side. Each cuboid (CB1) has graduated broaches (B1) for ridges (URi and URo) of CR1 at upper surface (US1) and graduated broaches (B2) for ridges (RLo and RLi) of CC2 on lower surface (LS1).

Figure 7B:
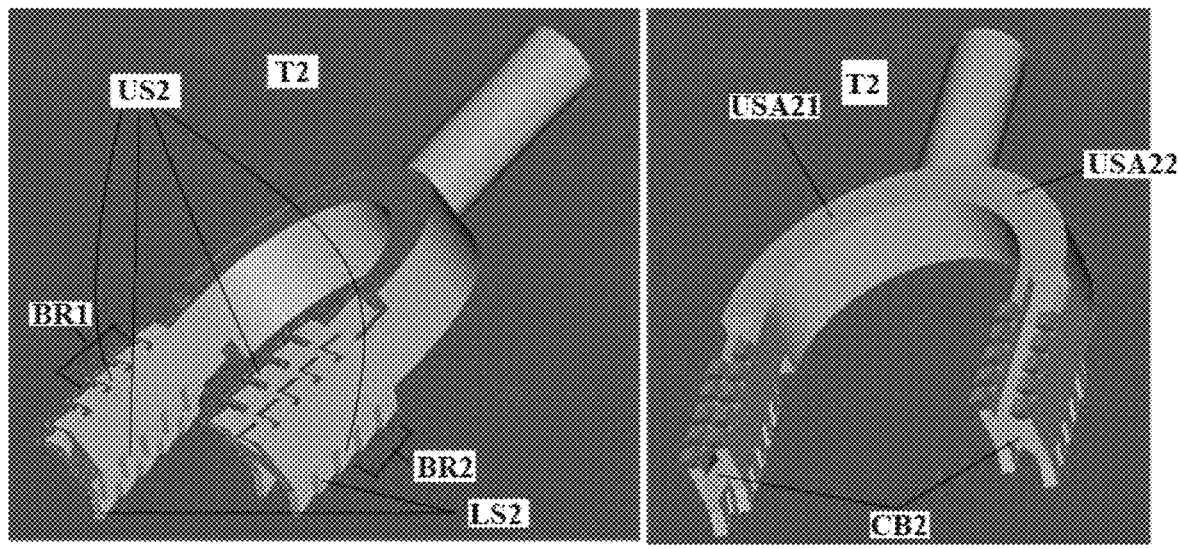

Another tool (T2) is also a hand tool (FIG. 7B) with two arms (UA21 and UA22) for making final cuttings in the form of grooves in CR1 and CC2 facets. Both the ends of arms (UA21 and UA22) terminate as cuboids (CB2) which are at an angle of 30 degrees to the horizontal. These cuboids (CB2) which are at an angle of 30 degrees to the horizontal and are sized about 17 mm in length, 7 mm height and 8 mm wide. The inner edge of cuboids (CB2) is higher up than the outer on either side. Each cuboid (CB2) has regular broaches (BR1) for ridges of CR1 at upper surface (US2) and regular broaches (BR2) for ridges of CC2 on lower surface (LS2).

The U at its base would have adjusting screw to vary the distance between 2 arms.

The tool (T1) with graduated broaches is just for marking the position of the grooves and making rough cut through the hard cortical shell of bone without fracturing it. The tool (T2) comprising of regular broaches is different than that comprising of graduated broaches as it is used to finally cut grooves of requisite size for fixing the ridges of implant.

Yet another tool with arms similar to above tools would hold the both right and left CR1 and CCL2 together and insert it into the joint space and grooves created.

We cannot use a single tool which can graduate as well as cut because the bone has two layers; outer hard cortical layer and relatively softer inner layer. It is important to cut the cortical layer first with sharp cuts followed by cutting of inner softer layer. If a regular broach is used alone it would fracture the bone rather than cutting it. Using the graduated broach would create partially formed grooves.

Method to Use of the Present Invention:

Step 1: Reduction of dislocation by drilling the facets flat and parallel to each other. The drilling needs to be adequate enough to house the implant (2 mm width of each facet).

Step 2: Rough grooves for fixing the ridges in CR1 and CC2 are prepared using the tool T1 followed by finishing of the grooves using the tool T2.

Step 3: An instrument holding bilateral implants 18 mm apart, would place it within the opened joints simultaneously. The implants would be hammered into bilateral joint spaces with ridges fitting in the grooves created by the broaches using tools T1 and T2.

Step 4: Once the implants are in position, fixing of CR1L on one side (Say Left) with the help of normally available Fixation screws through the hole provided in to insert it in atlas (C1). Another screw would fix the CC2L in axis (C2) facet. Similarly, screws would fix CR1R and CC2R on Right atlas (C1) and axis (C2) respectively.

It is obvious that the surface of implant coming in contact with bone would be rough with ratchets to prevent it from moving out. The surfaces may be sprayed with substances that enhance osseo-integration. The interacting surfaces between CR1 and CC2 (the spherical portions and the channel and rail) would be highly polished. The components can be made of titanium/cobalt-chrome or PEEK or some other strong inert substance or a combination of these or any suitable material, to prevent the metal loss that is likely to occur in a metal on metal surface.

In another embodiment, the interacting surfaces may be flat (CR1 undersurface) on convex (CC2 upper surface) instead of convex on convex. This would make the joint slightly more stable but at the cost of the coupling movement. A cone on cone model (concave on convex) is a feasible and is extremely stable; but is not gyroscopic and has the disadvantage of not being adaptable to varying coronal angles. This would make the implant less universal.

In yet another embodiment, (referring to FIG. 8), the implant is made of 2 inter-digitating components called Circular Connector Leg 1 (CCL1) suitable for fixing in Axis (C2) and Circular Connector Leg 2 (CCL2) suitable for fixing in Atlas (C1). CCL1 acts like a channel and CCL2 acts like a corresponding railing.

The railing and the channel is along the circumference of a circle, the center of which is odontoid. Such circular railings can provide only circular motion in clockwise and anti-clockwise direction, but cannot allow any other motion including slipping of C1-C2. This provides stability in atlanto-axial joint without compromising the circular motion.

The railing has a constriction in the form of a narrow neck as compared to the fundus with a similar corresponding channel. This prevents the railing to come out from the channel.

Two sets of each such implant comprising CCL1 and CCL2 together are fixed on both sides (left and right) simultaneously along the circumference of the C1-C2 joints.

Figure 8:
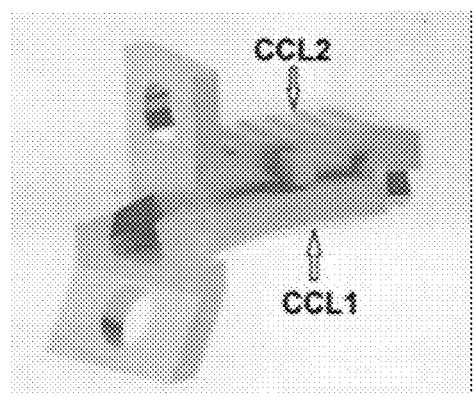
FIG. 8A: Detailed front view of Connector Leg 1
  Numbering:
  100L: Locking blocks
  100P: Plate which will rest on Pars-Inter-articularis 100C: Solid curved section of the Connector leg 1
100H: Circular Hole for pedicle screw fixation
100R: Channel for fitting Connector Leg 2
100W: Width of channel 100R.
100BW: Total width of the Connector Leg 1 as seen from below
100T: Solid section below Channel 100 R
FIG. 8B: Front view of Connector Leg 1
Numbering:
100B: Locking Ratchets in the form of Serrations at the bottom of the Connector Leg 1
100P: Plate which will rest on Pars-Inter-articularis
100PW: Width of the Plate 100P
100L: Locking blocks
FIG. 8C: Exploded side view of 100B
100H: Circular Hole for pedicle screw fixation
100BL: Circumference of circular section of Channel 100R
100BW: Total width of the Connector Leg 1 as seen from below
100R1: Inner Radius of the Circular Connector Leg 1 (CCL1)
100R2: Outer Radius of the Circular Connector Leg 1 (CCL1)
FIG. 8D: Front view of Channel 100R
100RC: Constriction in upper part of channel 100R

Referring to the accompanying drawings and figures, FIG. 8 shows the complete assembly of the implant of this embodiment. Circular Connector Leg 1 (CCL1) fixed on the Axis (C2) is so designed so as to keep the natural anatomical shape of the Axis in mind which is responsible for the movement of the neck.

Figure 8A:
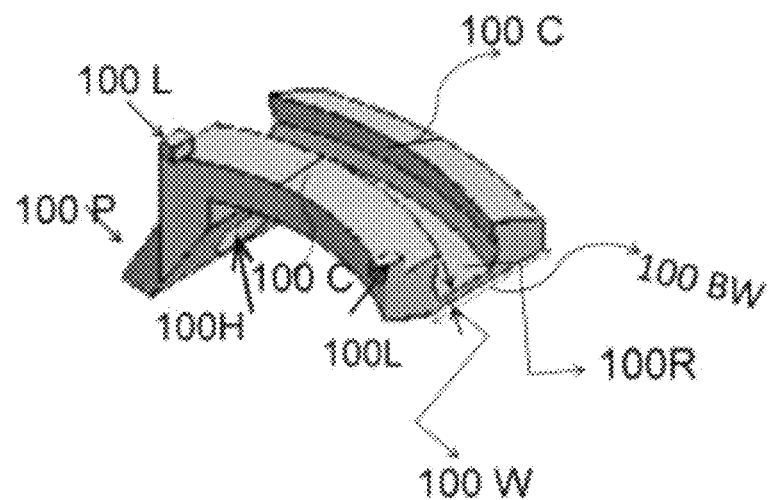

Referring to FIG. 8A:

CCL1 comprises of an arc shaped body which has a channel like shape in the centre. The curve of the arc is designed keeping in view the normal human anatomical structure of Axis C2. The inner radius of the arc is 14.64 mm and the outer radius is 25.23 mm. This gives a total width 100BW of CCL1 as (25.23−14.64=10.59 mm). More precise dimensions of the curve of the arc is calculated with the help of radiography of individual patient. The upper part of the CCL1 has a solid curved section 100C out of which the channel 100R has been cut leaving behind a solid section of thickness 1.5 mm. Channel 100R for fitting CCL2 is broader at the base and gets constricted towards the top end so as to stop the vertical movement of railing once it is slid in the channel. Solid curved section 100C has locking blocks 100L at the ends to prevent sliding of the railing of CCL2 forward and backward out of the channel of CCL1, once fitted. A plate 100P is provided at the bottom and towards left end of the CCL1. This plate helps to provide stability to CCL1 and rests on Pars-articualris region of the Axis.

Referring to FIG. 1, the Pars-articualris of the Axis is naturally inclined at an angle of 150 degree from the flat surface of atlanto-axial Joint. Therefore, the angle at which the plate 100R is bent outward is 150 degree so as to fix it in the Pars-articualris of the Axis C2 in the best suitable position. The plate 100R has a circular hole 100H in it to accommodate a normally available pedicle screw of width 3.5 mm and length 16-18 mm which is required to fix the CCL1 in the Axis. Vertical height of the plate 100R is 4.20 mm carefully selected to suit the above said pedicle screw. The optimum thickness 100PW of the plate 100R is 2.31 mm which can prevent bending of the plate 100R after fixing the pedicle screw.

Figure 8B:
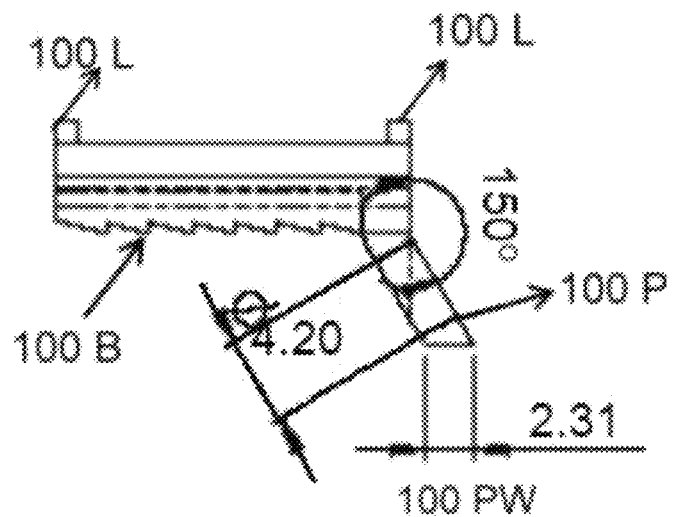
Figure 8C:
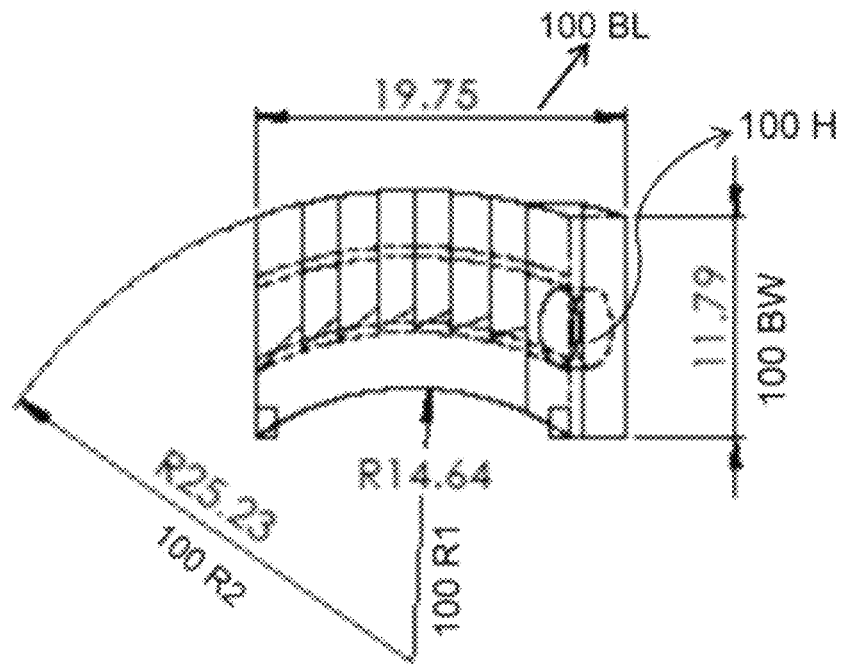

Referring to FIGS. 8B and 8C, the bottom face of the CCL1 comprises locking ratchets 100B in the form of serrations. These serrations are required for fitting the implant on the body of the Axis C2 by routine method using a soft hammer. The total curved length or the circumference of circular section (100BL) of the serrations is 19.75 mm. The inner radius 100R1 and the outer radius 100R2 are shown as 14.64 and 25.23 respectively which are the corresponding to curve of the arc of CCL1. The width as shown by 100BW in FIG. 8C corresponds to the total width of the CCL1 as seen from the bottom view of CCL1.

Figure 8D:
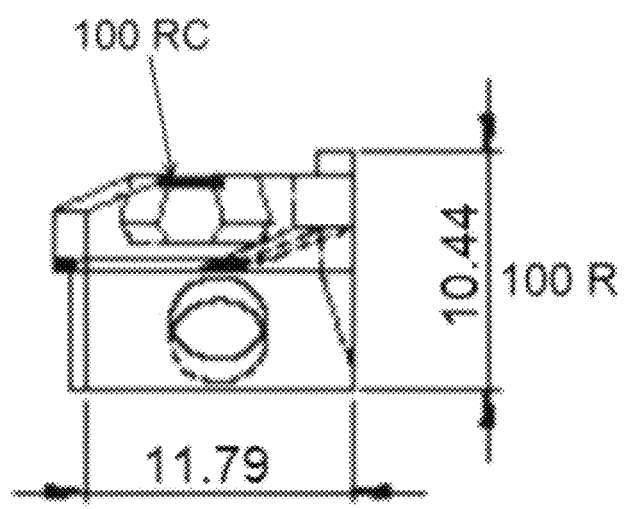

Referring to FIG. 8D, the channel 100R is constricted at the upper end (100RC) to avoid sliding out of the railing of CCL2, in vertical direction, once it is fitted in the channel groove of CCL1.

Figure 9A:
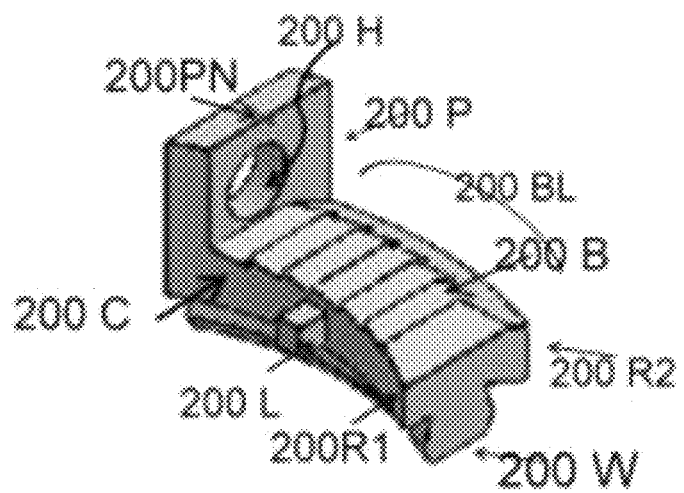
FIG. 9A: Detailed front view of Connector Leg 2
Numbering:
200L: Locking block
200P: Plate which will rest on isthmus of C2
200C: Solid curved section of the Connector leg 2
200H: Circular Hole for pedicle screw fixation
200R: Rail for fitting Connector Leg 2 in Channel 100R of Connector Leg 1
200W: Width of channel 200R
200B: Locking Ratchets in the form of Serrations at the top of the Connector Leg 2
FIGS. 9B, 9C and 9C(1): Views indicating dimensions of Locking Ratchets

Design and Constructional Features of CCL2:

Referring to FIGS. 9A,B,C and D, the CCL2 consists of a rail 200R which is cut in a shape suitable for fitting in the channel of CCL1. FIG. 9D describes the dimensions of constriction in the rail 200R which will best fit in the channel 100 R of the CCL2. Constriction in upper side again prevents the railing to come out of CCL1. Therefore, the channel constriction and the Railing constriction get locked with each other once inserted through side groove of the channel. The railing thus can not move out vertically due to this locking arrangement.

To prevent the railing slip horizontally out of the channel, there is provided a Locking Block 200L at the top outer edge of the railing. When the railing moves horizontally and in circular manner inside the channel, it is stopped at the ends by Locking blocks 100L in CCL1 due to the fixing of Locking Block 200L of the railing. Therefore, the railing, cannot move out horizontally also once fitted.

CCL2 also uses a plate 200P which will rest on back side of the lateral mass of Atlas C1 and fixed with a screw that provides stability to CCL2.

The angle at which the plate 200R is bent outward is 150 degree so as to fix it in the best suitable position. The plate 200R has a circular hole 200H in it to accommodate a normally available pedicle screw of width 3.5 mm and length 16-18 mm which is required to fix the CCL2 in the Atlas. Vertical height of the plate 200R is 4.20 mm carefully selected to suit the above said pedicle screw. The optimum thickness 200PW of the plate 200R is 2.31 mm which can prevent bending of the plate 200R after fixing the pedicle screw.

Figure 9B:
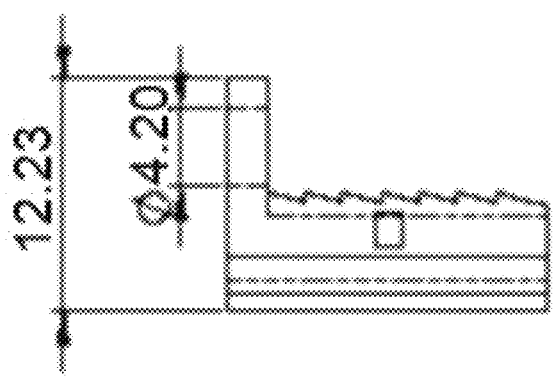
FIG. 9D: Exploded view of Rail 200R
100RC: Constriction in upper part of channel 100R
Figure 9C:
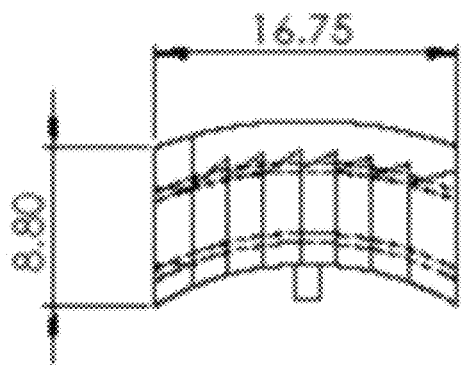
Figure 9D:
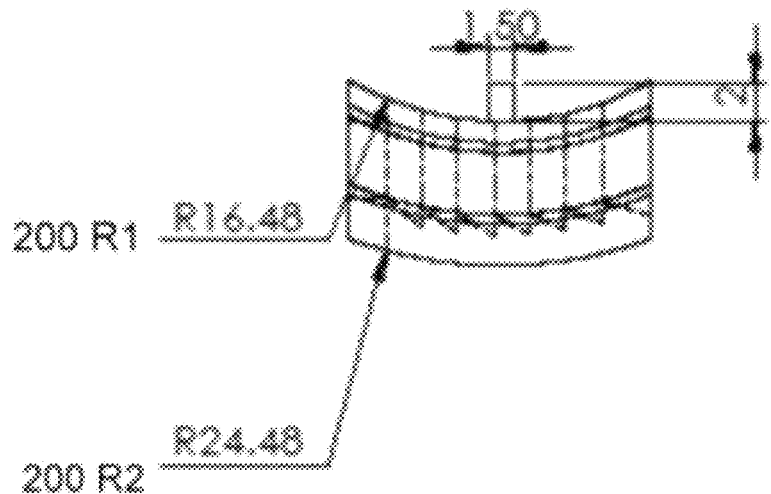
Figure 9D:
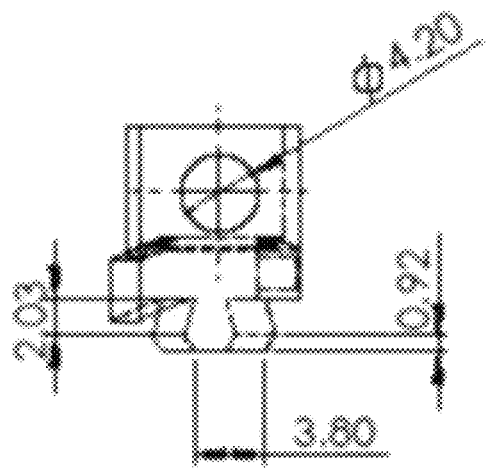

Referring to FIGS. 9B and 9C and 9C(1), the bottom face of the CCL2 comprises locking ratchets 200B in the form of serrations. These serrations are required for fitting the implant on the body of the Axis C2 by routine method using a soft hammer. The total curved length or the circumference of circular section (200BL) of the serrations is 16.75 mm. The inner radius 200R1 and the outer radius 200R2 are shown as 16.48 mm and 24.48 mm respectively which are the corresponding to curve of the arc of CCL2.

Figure 10:
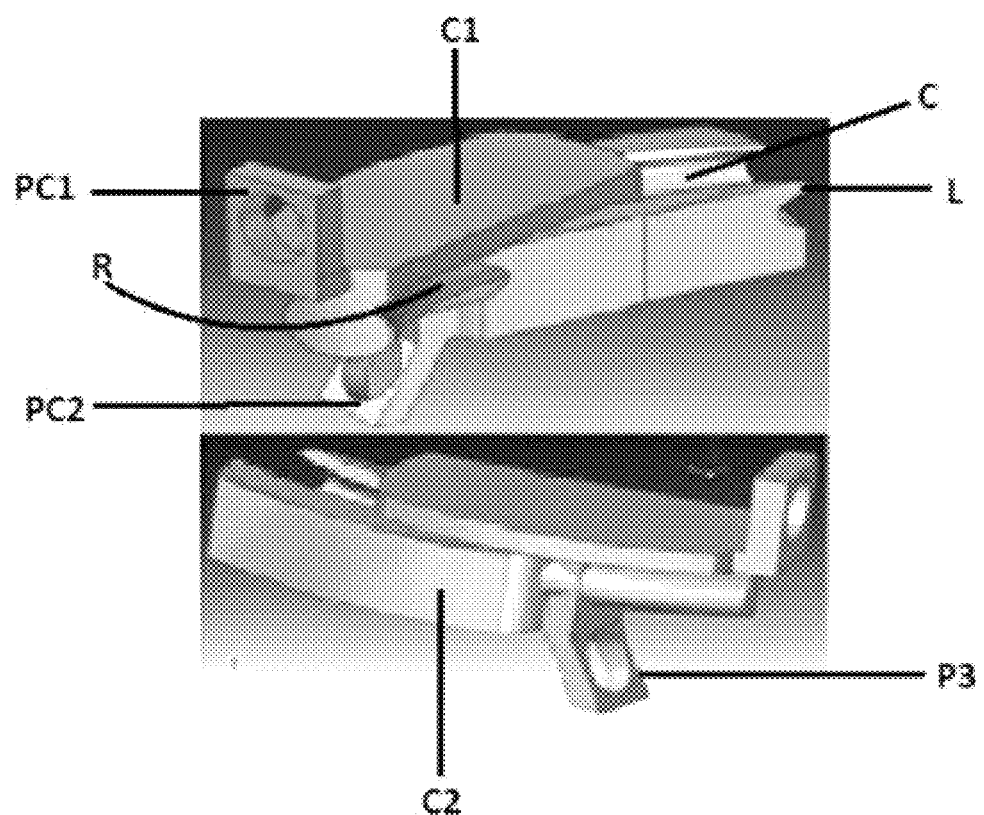
FIG. 10: Possible Embodiment of the present invention (circular rail and channel in the main interacting surface)
C1: C1 component
C2: C2 component
R: Railing
C: Channel
L: Lock
PC1: Plate for screw in C1 component
PC2: Plate for screw in C1 component

Such design has a limitation of being used only in a particular coronal angle. Hence has to be made according to an individual's coronal angle. Since the channels and railings have to be along a circumference of a circle whose center is the odontoid, therefore as a further embodiment to this, railing and the corresponding channel can be circular in cut section instead of a pentagon (FIG. 10). With some play, the implant becomes slightly more gyroscopic, adapting to different anatomies of the joint.

In one more embodiment, there could be two railings and channels in each implant. This would reduce the height of the implant.

In yet another embodiment, the channel floor may be laden with ball bearings of smaller diameter than the channel diameter. The railing would be of smaller height than the one described in FIG. 9. The height of the railing along with the diameter of the ball bearing would be equal to the railing height described in FIG. 9 (2.03). This would make the movement of railing within the channel smooth. The ends of the channels need to be partially closed to allow only the entry of railing but prevent the falling of ball bearings.

Novelty:

Till date, the inventor has not come across any implant for atlanto-axial C1-C2 joint implant which can give freedom of movement to the neck close to natural movement of the neck. There is no atlanto-axial joint implant which can be used for treating congenital abnormalities or inflammatory arthritis with settling apart from traumatic AAD. Also, no implant exists to provide all the degrees of freedom of movement seen in natural C1-2 joints.

The present invention, with the help of a novel concept of using circular Channel and Railing arrangement along with two opposing convex (or convex on flat surface), can successfully overcome all the above limitations. The channel and rail can be on the side or along the opposing surface Hence the invention seems novel to the best of the knowledge of the inventor.

Inventive Step:

To achieve novelty, the inventor has put in considerable effort to design and develop the implant of the present invention which can be fitted post reduction from the back of the neck avoiding the infected oral cavity route. It can mimic the natural normal movement of the neck in Right-Left directions since the arcs of the channel and railings or any other mechanism used for the purpose such as opposing discs or disc on disc, are designed keeping in view normal human anatomical structure of C1-C2 joints. The implant can thus gives multiple degrees of freedom for neck movements.

It can mimic the natural normal movement of the neck of turning to either sides. The channel and railing implant with play does provide some antero-posterior or lateral translational or bending movement at C1-2. This channel and railing implant is stable. The sphere on sphere model of C1-2 implant provides some lateral and flexion-extension movements. In fact, the rotational movement is associated with coupling vertical movement, closest to the normal.

With the rail and channel alone (model 2) the stability is high but it compromises the natural translational and coupling movement. For patients suffering from Congenital AAD due to deformity in C1-C2 joints can be helped, as this implant takes care of an individual's anatomical structure of the joint and can be easily manufactured by the implant manufacturer.

Hence the invention carries a technological advancement in the field of implants and duly covers the inventive step.

INDUSTRIAL APPLICATION

Since the present invention pertains to the field of surgical and medical implants, it has a lot of societal and commercial significance. It can help save lives of many patients suffering from AAD. It can even treat congenitally deformed patients with AAD, since it can be easily manufactured by any existing implant manufacturer by taking the dimensions of C1-C2 joints of an individual patient with the help of radiography. Hence, the present invention has industrial application.

In the preceding detailed description, the invention is described with reference to exemplary drawings thereof. Various modifications and changes may be made thereto without departing from the broader spirit and scope of the invention as set forth in the description. The specification and drawings are accordingly, to be regarded in an illustrative rather than a restrictive sense. Thus without analysis, the foregoing will so fully reveal the gist of the present invention that others can, by applying current knowledge, readily adapt it for various applications without omitting features that from the standpoint of prior art, fairly constitute essential characteristics of the generic or specific aspects of this invention.

I claim:

1. An artificial implant (artificial joint) for atlas-axis (C1-2) lateral joints comprising two sets of inter-digitating components called Circular rail (CR1) suitable for fixing in atlas (C1) and Circular channel (CC2) suitable for fixing into axis (C2) wherein:

Circular rail (CR1) and the Circular channel (CC2) is fitted along the circumference of an imaginary circle, the center of which is an odontoid; to provide rotational movement almost close to normal;

interacting surfaces of the implant are convex on convex to provide a gyroscopic motion with small degree of lateral and translational movement;

gyroscopic design makes the implant (joint) universal adapting to varying angles and orientation of C1-2 joints of different individuals;

interacting surfaces of the implant are convex on convex to provide coupling (vertical translation on rotational movement); and implant is designed to be fitted from the back of the neck with help of hand tools (T1 and T2) and fixation screws.

2. The artificial implant for atlas-axis (C1-2) lateral joints as claimed in claim 1, wherein implants are fixed on both sides of C1-2 joint simultaneously along the circumference of an imaginary circle, the center of which is the odontoid.

3. The artificial implant as claimed in claim 1, wherein Circular rail (CR1) suitable for fixing in atlas (C1) comprises an upper ledge (UL) and a lower ledge (LL) wherein
   inner edge (ULi) of the upper ledge (UL) is straight and is connected to Lower ledge (LL) with 3 mm thick connecting stalk (CS);
   outer edge (ULo) of the upper ledge (UL) is circular, corresponding to the circumference of circle with radius of about 20-23 mm;
   two projections or the locking pins (LP) are located at ends of the outer edge (ULo) of upper ledge (UL);
   a perpendicular plate (P1) with ⅔ of hole (H) is located on top portion;
   inferior or under surface of Lower ledge (LL) of Circular rail (CR1) is concave (CONC) with central spherical projection (CONV) making interacting surfaces of the implant sphere on sphere;
   lower ledge (LL) consists of a Monorail (MR) of width about 0.6 mm on its outer edge and follows the circumference of circle with center as odontoid and radius of 18-21 mm and a Groove (G) above the Monorail (MR) about 2-3 mm deep; and
   upper surface of upper ledge (UL) of circular rail (CR1) comprises ridges (Ro and Ri).

4. The artificial implant as claimed in claim 1, wherein Circular channel (CC2) suitable for fixing into axis (C2) comprises an fused upper half (UL2) and a lower half (LL2) wherein
   inner edge (UL2i) of the upper half (UL2) is straight and consists of a plate (P2) of 1.5 mm thickness and 4.2×4.2 mm width and height, angled at 60-70 degrees with respect to the plane of ground and a hole (H2) in the plate (P2);
   outer edge (UL2o) of the upper half (UL) is circular, corresponding to the circumference of circle with radius of about 20-23 mm and consists of a wall (W1) of 2.5 mm thickness and 2.5 mm height angulated at 60-70 degrees with respect to the plane of lower surface of CCL; and
   the lower surface of lower ledge (LL2) comprises ridges (RLo and RLi) with thickness and height of 2 mm each, running along its entire length at 60 degrees from the surface (perpendicular to plane of ground) fixed inside the Axis (C2) facets in a manner such that ridges (RLo) are positioned higher than the ridges (RLi).

5. The artificial implant comprising a Circular channel (CC2) suitable for fixing into axis (C2) wherein the Wall (W1) as claimed in claim 4 comprises a channel (CMR) in wall (W1) that houses the monorail (MR) of Circular rail (CR1), with an upward projection in the midpoint of its (CMR's) outer circumference acting as a locking pin (LP2) and is narrowest at the center and broadens along the outer lengths of its circumference.

6. The hand tool of claim 1 comprising two arms (UA1 and UA2) 5 cm long and 18 mm wide apart from each other and end in cuboids (CB1) on both ends, for making rough cuttings in CR1 and CC2 facets.

7. The hand tool (T1) as claimed in claim 6, wherein the cuboids (CB1):
   are at an angle of 20-30 degrees to the horizontal and are sized about 17 mm in length, 7 mm height and 8 mm wide;
   inner edge of cuboids (CB1) is higher up than the outer on either side; and
   each cuboid (CB1) has graduated broaches (B1) for ridges of CR1 at upper surface (US1) and graduated broaches (B2) for ridges of CC2 on lower surface (LS1).

8. The hand tool (T2) of claim 1 comprising two arms (UA21 and UA22) 5 cm long and 18 mm wide apart from each other and terminate as cuboids (CB2) on both ends, for making final cuttings in the form of grooves in CR1 and CC2 facets.

9. The hand tool (T2) as claimed in claim 8, wherein the cuboids (CB2):
   are at an angle of 20-30 degrees to the horizontal and are sized about 17 mm in length, 7 mm height and 8 mm wide;
   inner edge of cuboids (CB2) is higher up than the outer on either side; and
   each cuboid (CB2) has regular broaches (BR1) for ridges of CR1 at upper surface (US2) and regular broaches (BR2) for ridges of CC2 on lower surface (LS2).

10. A method of use of the artificial implant for atlas-axis (C1-2) lateral joints as claimed in claim 1, comprising the steps of:
    fixing CR1 on right and left sides, inter-digitating with the CC2 on each side so that the monorail (MR) (edge of lower ledge of CR1) and the channel of CC2 on each side provides approximately 23 degrees of translational and angular movement on either side, in unison and in either clockwise or anticlockwise direction; and
    restricting the movement of monorail at its maximum limit by the locking pins (LP 15 and LP2).

11. The artificial implant for atlas-axis (C1-2) lateral joints as claimed in claim 1, wherein railing and the corresponding channel can be circular in cut section with some tolerance (play) making it gyroscopic for adapting to different anatomies of the joint.

12. The artificial implant for atlas-axis (C1-2) lateral joints as claimed in claim 1, wherein there are two railings and channels in each implant to reduce the height of the implant.

13. The artificial implant for atlas-axis (C1-2) lateral joints as claimed in claim 1, wherein:
    ball bearings of smaller diameter than the channel diameter are in contact with the channel floor to reduce the height of the railing;
    ends of the channels are partially closed to allow only the entry of railing but preventing the falling of ball bearings; and
    multiple rails and channels can be used to get the desired result.

14. The artificial implant for atlas-axis (C1-2) lateral joints as claimed in claim 11, wherein:
    ball bearings of smaller diameter than the channel diameter are in contact with the channel floor to reduce the height of the railing;
    ends of the channels are partially closed to allow only the entry of railing but preventing the falling of ball bearings; and
    multiple rails and channels can be used to get the desired result.

* * * * *